(12) United States Patent
Bochner et al.

(10) Patent No.: US 7,275,796 B2
(45) Date of Patent: Oct. 2, 2007

(54) DEVICE FOR FACILITATING MEDICAL EXAMINATION

(76) Inventors: Ronnie Z. Bochner, 10 Candle La., East Brunswick, NJ (US) 08816; Andrew Lewis Wright, 3530 Meadowcroft, Kalamazoo, MI (US) 49004; Michael Stephen Rozewicz, 7335 Kendall Arbor, Kalamazoo, MI (US) 49009; Kris Douglas Eager, 1351 W. Gull Lake, Richland, MI (US) 49083

(*) Notice: Subject to any disclaimer, the term of this patent is extended or adjusted under 35 U.S.C. 154(b) by 458 days.

(21) Appl. No.: 10/366,950

(22) Filed: Feb. 13, 2003

(65) Prior Publication Data
US 2004/0160147 A1    Aug. 19, 2004

(51) Int. Cl.
A47B 81/00 (2006.01)
A47B 46/00 (2006.01)
A47B 7/00 (2006.01)
A47C 20/02 (2006.01)

(52) U.S. Cl. .............. 312/209; 312/249.11; 5/624; 5/649

(58) Field of Classification Search ........... 312/209, 312/235.3, 235.2, 249.1, 249.8, 249.9, 249.11, 312/249.12, 249.13; 5/624, 649
See application file for complete search history.

(56) References Cited

U.S. PATENT DOCUMENTS

| | | | |
|---|---|---|---|
| 658,999 A * | 10/1900 | Scannel | 312/209 |
| 724,125 A * | 3/1903 | Prindle | 108/6 |
| 804,089 A * | 11/1905 | Blanc | 312/249.12 |
| 1,409,330 A * | 3/1922 | Aper | 312/228 |
| 1,568,498 A * | 1/1926 | Caliver | 312/235.3 |
| 1,943,282 A * | 1/1934 | Bellavia | 312/222 |
| 2,678,461 A * | 5/1954 | Stanley | 15/265 |
| 2,679,445 A * | 5/1954 | Roehm | 312/209 |
| 2,692,812 A * | 10/1954 | Stahl | 312/310 |
| 2,963,332 A * | 12/1960 | Breuning | 312/231 |
| 3,016,275 A * | 1/1962 | Grant | 312/209 |
| 3,085,842 A | 4/1963 | Johnson | |
| 3,334,951 A | 8/1967 | Douglass, Jr. et al. | |
| 3,428,383 A | 2/1969 | Nobel | |

(Continued)

FOREIGN PATENT DOCUMENTS

DE    3015644 A    10/1981

(Continued)

OTHER PUBLICATIONS

U.S. Appl. No. 10/545,033 on "Device for Facilitating Medical Examination" (U.S. National Phase of International Patent Appln. No. PCT/US2004/004431) filed Aug. 11, 2005, Inventors: Ronnie Z. Bochner, Andrew L. Wright, Michael S. Rozewicz and Kris D. Eager.

(Continued)

*Primary Examiner*—David Dunn
*Assistant Examiner*—Sarah B. McPartlin
(74) *Attorney, Agent, or Firm*—Greenberg Traurig, LLP (57) ABSTRACT

A device for facilitating a medical examination includes a movable body having a storage compartment therein and a door member movably mounted to the body for at least partially covering the storage compartment. A supporting unit is mounted to the body for supporting a foot of a patient during the performance of a medical examination.

21 Claims, 6 Drawing Sheets

U.S. PATENT DOCUMENTS

| | | |
|---|---|---|
| 3,715,148 A | 2/1973 | Beals |
| 3,966,286 A | 6/1976 | Groseclose |
| 4,114,965 A | 9/1978 | Oye et al. |
| 4,736,998 A | 4/1988 | Wilson et al. |
| 5,184,601 A | 2/1993 | Putman |
| 5,299,338 A | 4/1994 | Foster |
| 5,399,007 A | 3/1995 | Marconet |
| 5,405,587 A | 4/1995 | Fernandez et al. |
| 5,518,310 A | 5/1996 | Ellman et al. |
| 5,547,270 A | 8/1996 | Dang |
| 5,564,803 A | 10/1996 | McDonald et al. |
| 5,662,396 A | 9/1997 | Reeder et al. |
| 5,702,115 A | 12/1997 | Pool |
| 6,022,088 A | 2/2000 | Metzler |
| 6,619,768 B1 * | 9/2003 | Northrop et al. ........... 312/290 |
| D512,149 S | 11/2005 | Bochner et al. |

FOREIGN PATENT DOCUMENTS

| | | |
|---|---|---|
| GB | 403503 A | 12/1933 |

OTHER PUBLICATIONS

International Search Report and Written Opinion dated Jun. 24, 2005, issued in related International Patent Application No. PCT/US2004/004431.

International Preliminary Report on Patentability dated Feb. 1, 2005, issued in related International Patent Application No. PCT/US2004/004431.

\* cited by examiner

DEVICE FOR FACILITATING MEDICAL EXAMINATION

FIELD OF THE INVENTION

The present invention relates to medical examination devices and, more particularly, to a device adapted for facilitating a medical examination.

BACKGROUND OF THE INVENTION

Obstetric/gynecological examinations are typically performed on female patients while they lie on medical examining tables (see, e.g., U.S. Pat. Nos. 2,679,445 and 3,334,951). Prior to the performance of such an examination, the patient climbs on a medical examination table and places her feet on stirrups of the table. Due to their large size and bulkiness, these medical examination tables are not mobile. As a result, the conventional medical examination tables are not suitable for performing medical examinations on bed-bound patients.

Various movable cart-like devices have been developed for use in the medical field (see, e.g., U.S. Pat. Nos. 3,428,383, 3,715,148, 3,966,286, 4,114,965, 5,405,587, 5,564,803, 5,702,115 and 6,022,088). While these devices are adapted to carry various medical tools, equipment and/or supplies, they are not particularly suitable for performing an obstetric/gynecological examination.

SUMMARY OF THE INVENTION

The present invention overcomes the disadvantages and shortcomings of the prior art discussed above by providing a new and improved medical examination device. More particularly, the device includes a movable body having a storage compartment therein and at least one door member movably mounted to the body for at least partially covering the storage compartment. A supporting unit is mounted to the body for supporting a foot of a patient during the performance of a medical examination. Because of its mobility, the body can be placed adjacent a patient bed for performing a bedside medical examination.

BRIEF DESCRIPTION OF THE DRAWINGS

For a more complete understanding of the present invention, reference is made to the following detailed description of an exemplary embodiment of the present invention considered in conjunction with the accompanying drawings, in which.

DETAILED DESCRIPTION OF THE EXEMPLARY EMBODIMENT

Figure 1:
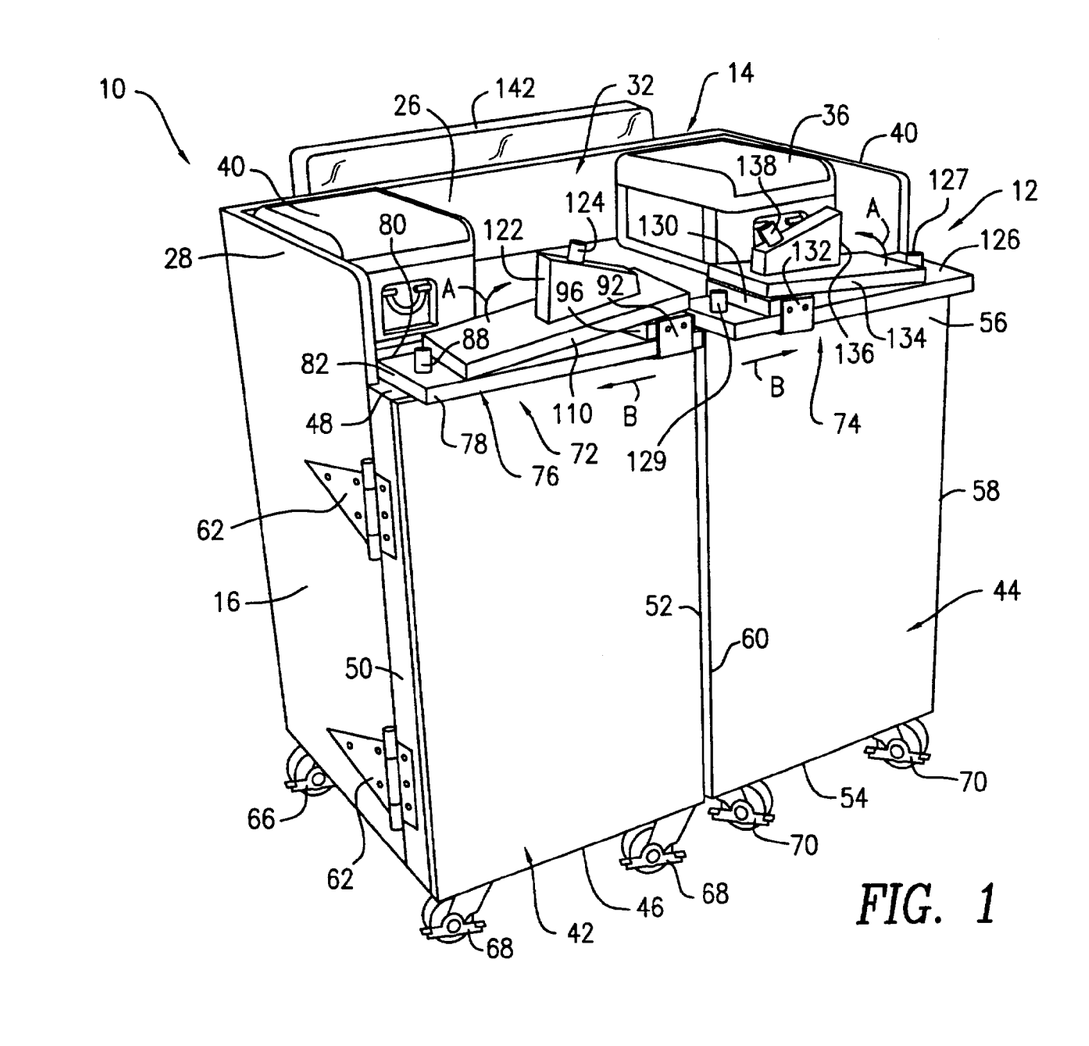
FIG. 1 is a front perspective view of a medical examination device constructed in accordance with the present invention and having a pair of door panels.

FIG. 1 illustrates a medical examination device 10 constructed in accordance with the present invention. More particularly, the device 10 includes a movable cart or body 12 having a rear vertical panel 14 (see FIG. 5) and a pair of lateral vertical panels 16, 18 (see FIGS. 1 and 2), both of which are attached to the rear panel 14. A lower support panel 20 (see FIG. 2) is mounted to the rear and lateral panels 14, 16, 18 adjacent lower ends thereof, while an upper support panel 22 (see FIG. 2) is attached to the rear and lateral panels 14, 16, 18 adjacent upper ends thereof. Each of the lower and upper support panels 20, 22 is oriented in a substantially horizontal manner so as to define a supporting surface for supporting various equipment utilized in the device 10. The rear panel 14, the lateral panels 16, 18 and the upper and lower support panels 20, 22 cooperate to define an interior storage space or compartment 24 (see FIG. 2) therebetween. The rear and lateral panels 14, 16, 18 also have upper portions 26, 28, 30 (see FIGS. 1, 2 and 3), respectively, all of which extend above and cooperate with the upper support panel 22 so as to define an exterior storage space 32.

Figure 2:
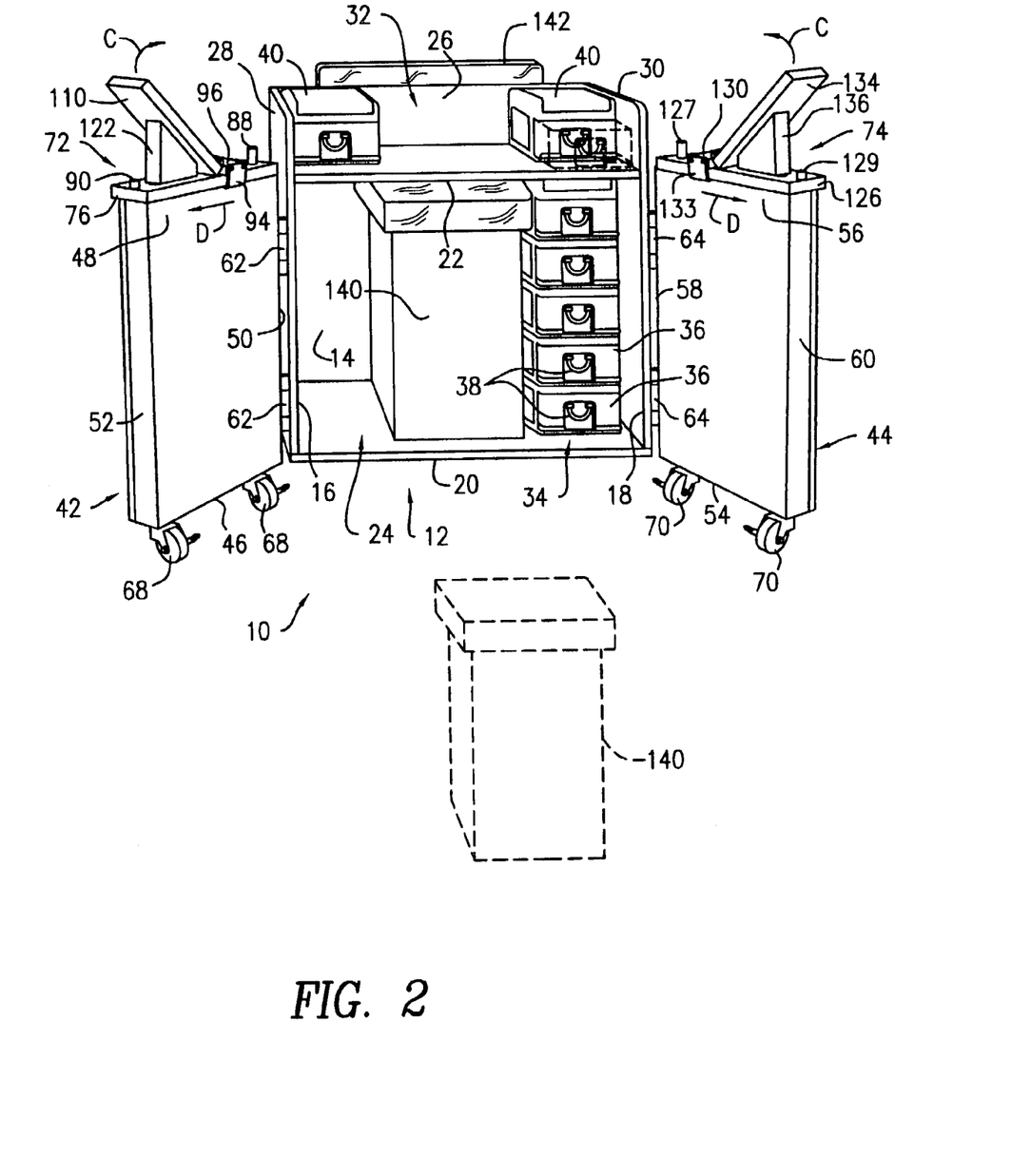
FIG. 2 is a perspective view of the medical examination device shown in FIG. 1, the door panels being illustrated in their open positions.

Referring to FIG. 2, a drawer assembly 34 is mounted in the storage space 24 adjacent the lateral panel 18. More particularly, the drawer assembly 34 includes a plurality of vertically stacked drawers 36 for storing various medical tools, supplies and other conventional items and materials (not shown) useful during the performance of a medical examination. Each of the drawers 36 has a handle 38 for use in pulling same from its closed position to its open position. Drawers 40 are also mounted in the storage space 32 (i.e., on the upper support panel 22) for providing additional storage area. Additional equipment, such as portable electric sources (e.g., batteries) and light sources (e.g., fiber optic lights and flexible light units), can be carried onboard in the storage space 24 and/or the storage space 32.

Referring now to FIGS. 1 and 2, the cart 12 is also equipped with a pair of door panels 42, 44. The door panel 42 has lower and upper ends 46, 48 and a pair of opposing sides 50, 52, while the door panel 44 has lower and upper ends 54, 56 and a pair of opposing sides 58, 60. Hinges 62 connect the side 50 of the door panel 42 to the lateral panel 16, while hinges 64 connect the side 58 of the door panel 44 to the lateral panel 18. In this manner, each of the door panels 42, 44 is pivotable between a closed position, in which it closes off the storage space 24, and an open position, in which it is swung pivotally outwardly from the cart 12. Releasable locking mechanisms (not shown) can be provided on the door panels 42, 44 and/or the lower and upper support panels 20, 22 such that the door panels 42, 44 can be releasably maintained in their closed positions.

Figure 5:
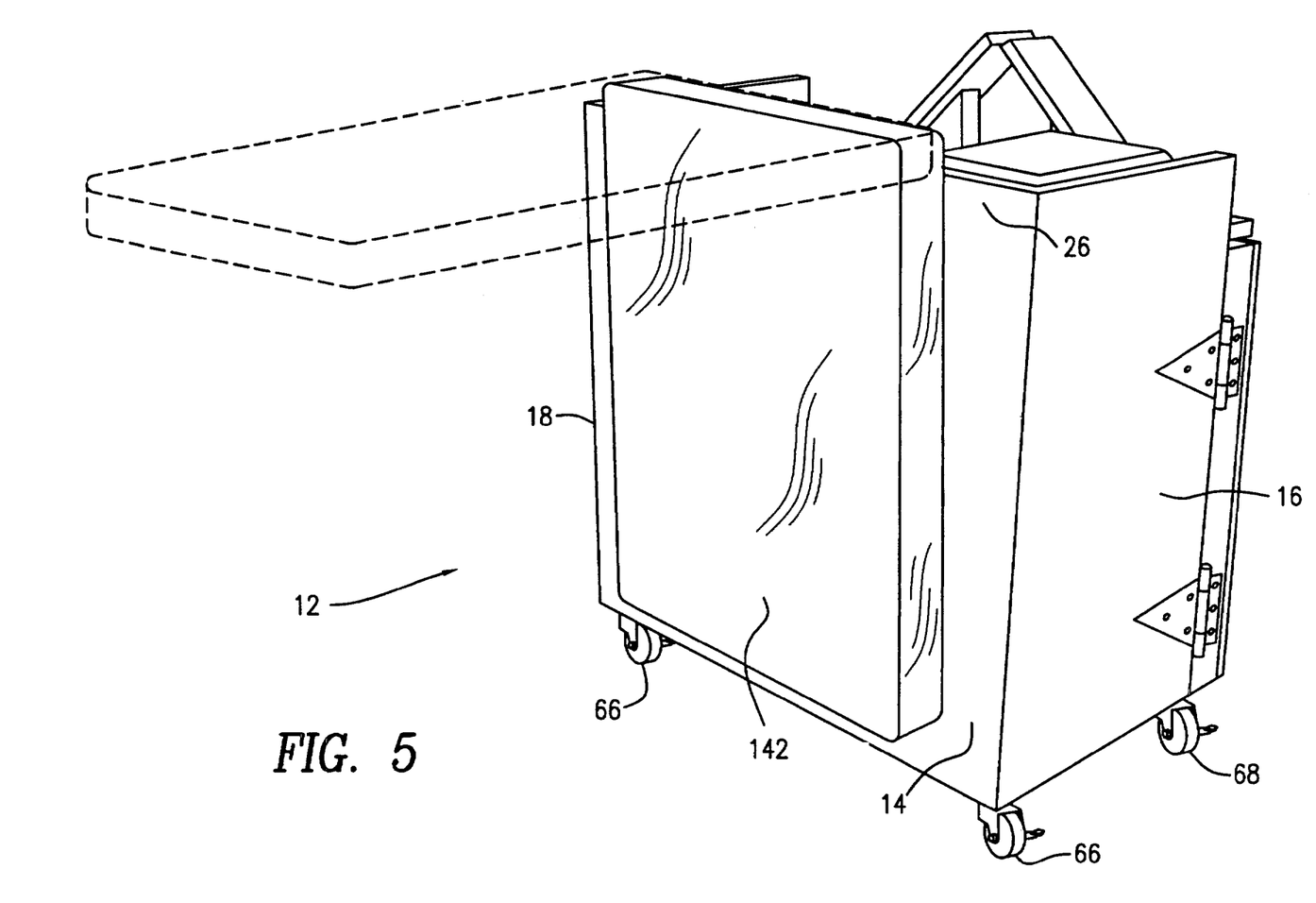
FIG. 5 is a rear perspective view of the medical examination device shown in FIGS. 1 and 2.

With reference to FIGS. 1, 2 and 5, the cart 12 includes wheels 66, 68, 70 (e.g., castor wheels) for supporting the cart 12 on a supporting surface (e.g., a floor). More particularly, the wheels 66 are attached to the lower support panel 20 adjacent the rear panel 14, while the wheels 68 and the wheels 70 are attached to the lower ends 46, 54, respectively, of the door panels 42, 44, respectively. Due to the wheels 66, 68, 70, the cart 12 can be easily moved to a desired location. The wheels 68 and the wheels 70 also facilitate the opening and closing of the door panels 42, 44, respectively.

Now referring to FIGS. 1-4, foot support assemblies 72, 74 are carried on the door panels 42, 44, respectively. More particularly, the foot support assembly 72 includes a rail member 76 fixedly attached to the upper end 48 of the door panel 42. The rail member 76, which has a pair of opposing sides 78, 80 and a pair of opposing ends 82, 84, includes a plurality of mounting holes 86 arranged in a substantially linear fashion along the longitudinal axis of the rail member 76. Retainer posts 88, 90 are mounted on the rail member 76 adjacent the ends 82, 84, respectively, for purposes to be discussed hereinafter.

Still referring to FIGS. 1-4, the foot support assembly 72 includes a pair of L-shaped brackets 92, 94 and a support block 96, which has a pair of opposing sides 98, 100 (see FIG. 4) aligned substantially with the sides 78, 80, respectively, of the rail member 76. The support block 96 is movably mounted on the rail member 76, while the brackets 92, 94 have vertical plates 102, 104, respectively, which are attached to the sides 98, 100, respectively, of the support block 96, and horizontal plates 106, 108, respectively, which are movably positioned between the rail member 76 and the upper end 48 of the door panel 42. In this manner, the brackets 92, 94 capture the rail member 76 therebetween so as to permit movement of the support block 96 along the longitudinal axis of the rail member 76.

Still referring to FIGS. 1-4, the foot support assembly 72 includes a foot rest 110 having a pair of ends 112, 114. The foot rest 110 includes a foot-resting surface 116 and a supporting surface 118 opposite the foot-resting surface 116. The end 112 of the foot rest 110 is pivotally attached to the support block 96 via a hinge 120 such that the foot rest 110 is pivotable between a folded-down position, in which the foot rest 110 is laid generally flat against the rail member 76 and hence the upper end 48 of the door panel 42 (see FIG. 1), and an unfolded position, in which the foot rest 110 extends upwardly from the rail member 76 and hence the door panel 42 in a slanted direction for supporting a patient's foot (see FIGS. 2, 3 and 5). A wedge-shaped support member 122 is attached to the supporting surface 118 of the foot rest 110 for maintaining the foot rest 110 in its unfolded position. Due to its attachment to the support block 96, the foot rest 110 is movable along the longitudinal axis of the rail member 76 conjointly with the support block 96. As a result, the foot rest 110 can be positioned in its unfolded position at one of a plurality of locations along the rail member 76 and hence the door panel 42. That is, the position of the foot rest 110 relative to the door panel 42 is adjustable. A retainer pin 124 projects from the support member 122 in a direction away from the foot rest 110. The retainer pin 124 is sized and shaped so as to be received in one of the mounting holes 86 of the rail member 76 when the foot rest 110 is in its unfolded position, thereby maintaining the foot rest 110 in its unfolded position at a preselected location along the rail member 76 and hence the door panel 42.

The foot support assembly 74 is basically identical, in construction and operation, to the foot support assembly 72. In such circumstances, the construction and operation of the foot support assembly 74 will be discussed briefly hereinafter without describing the details thereof.

Figure 3:
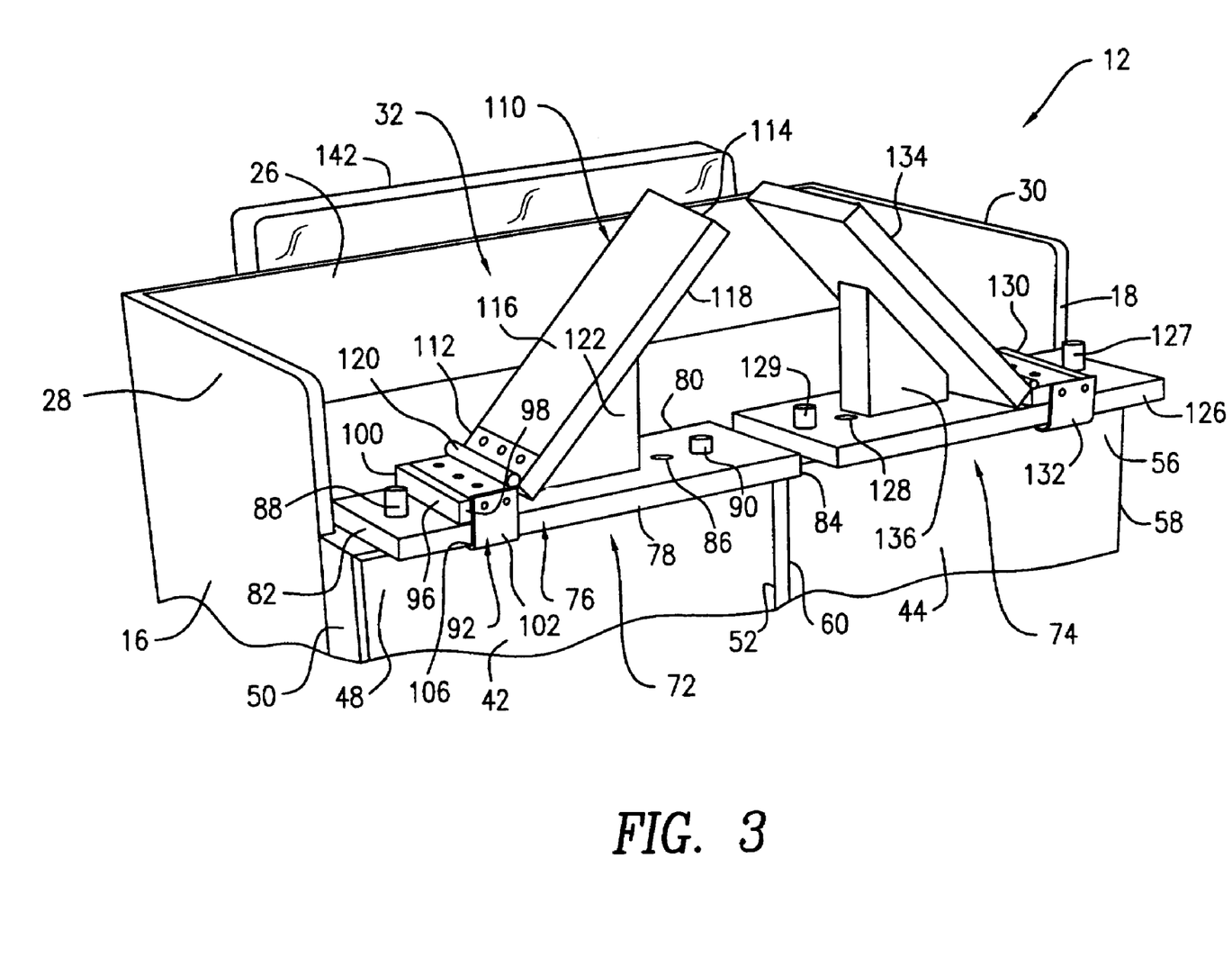
FIG. 3 is an enlarged perspective view of an upper portion of the medical examination device shown in FIGS. 1 and 2, illustrating its foot support assemblies.
Figure 4:
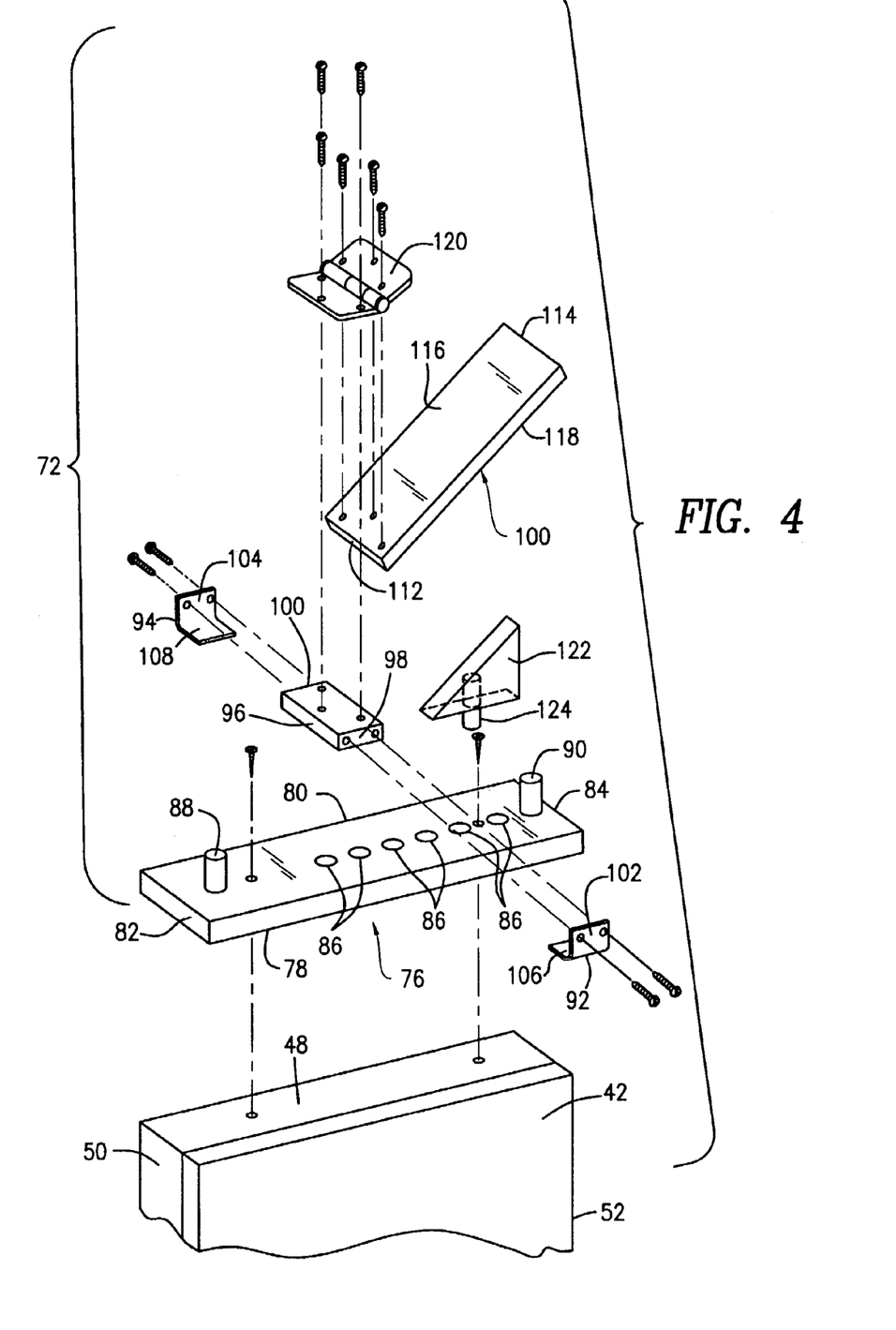
FIG. 4 is an exploded perspective view of one of the foot support assemblies shown in FIG. 3.

With reference to FIGS. 1-3, like the foot support assembly 72, the foot support assembly 74 is provided with a rail member 126 attached to the upper end 56 of the door panel 44 and having a plurality of mounting holes 128 (only one of which is shown in FIG. 3) and a pair of retainer posts 127, 129. A support block 130 is movably mounted on the rail member 126 via L-shaped brackets 132, 133, while a foot rest 134 is pivotally attached to the support block 130 such that it is pivotable between a folded-down position and an unfolded position. The foot support assembly 74 also has a support member 136, which is attached to the foot rest 134 for maintaining the foot rest 134 in its unfolded position. A retainer pin 138 projects from the support member 136 and is sized and shaped so as to be received in one of the mounting holes 128 of the rail member 126 for maintaining the foot rest 134 in its unfolded position at a predetermined location along the upper end 56 of the door panel 44.

Now referring to FIG. 2, the device 10 is also equipped with a stool (i.e., a seat member) 140. More particularly, the stool 140 is sized and shaped so as to be removably positioned in the storage space 24 of the cart 12 such that it is can be taken out from the store space 24 and used by medical personnel (e.g., a doctor) as a seat during the performance of a medical examination.

With reference to FIG. 5, a rigid support mat 142 is pivotally attached to the upper portion 26 of the rear panel 14. More particularly, the support mat 142 is sized and shaped so as to support a patient thereon during a medical examination. The support mat 142 is pivotable between an extended position, in which it extends in a substantially horizontal direction from the rear panel 14 of the cart 12 (see the broken line representation of the support mat 142 in FIG. 5), and a retracted position, in which it is oriented substantially horizontally and is laid against the rear panel 14 (see the solid line representation of the support mat 142 in FIG. 5).

Figure 6:
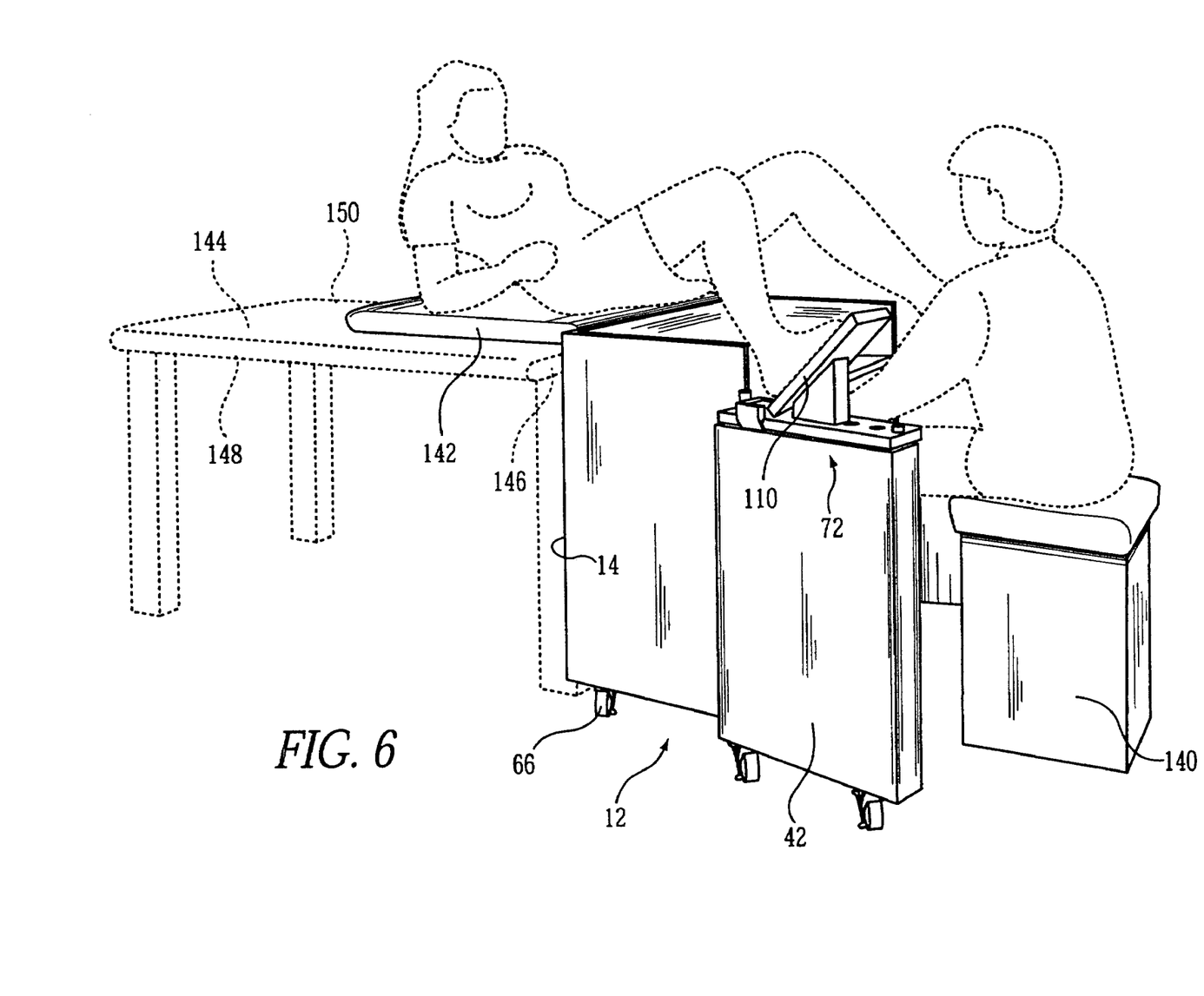
FIG. 6 is a schematic view of the medical examination device shown in FIGS. 1, 2 and 5, illustrating its use during a medical examination.

When the device 10 is not in use, it is stored away with the foot rests 110, 134 positioned in their folded-down positions and the support mat 142 positioned in its retracted position (see FIG. 1). Referring to FIG. 6, in order to perform a medical examination (e.g., an obstetric/gynecological examination) with the use of the device 10 alongside a patient bed 144 (e.g., a hospital bed) having a removable foot board (not shown) at an end 146 thereof, the foot board is removed. The cart 12 is then positioned against the end 146 of the bed 144. More particularly, with the supporting mat 142 placed and supported on the bed 144 in its extended position, the rear panel 14 of the cart 12 is positioned against the end 146 of the bed 144. Alternatively, the cart 12 can be placed against a side 148 or a side 150 of the bed 144. After properly positioning the cart 12, the wheels 66 are locked so as to prevent movement of the cart 12 relative to the bed 144. The door panels 42, 44 are then swung toward their open positions. Thereafter, the foot rests 110, 134 are pivoted from their folded-down positions toward their unfolded positions (as indicated by arrows A in FIG. 1) and are moved toward the sides 50, 58, respectively, of the door panels 42, 44, respectively, (as indicted by arrows B in FIG. 1) so as to position same at desired locations along the door panels 42, 44, respectively. In this regard, each of the retainer pins 124, 138 of the foot rests 110, 134, respectively, is inserted into a selected one of the mounting holes 86, 128 of the rail members 76, 126, thereby securing the foot rests 110, 134 to the rail members 76, 126, respectively, and hence the door panels 42, 44, respectively. A patient then places herself on the support mat 142 with her feet supported on the foot rests 110, 134 (see FIG. 6). While sitting on the stool 140, a medical personnel (e.g., a doctor) performs a medical examination (e.g., an obstetric/gynecological examination) on the patient.

After the use of the device 10, the foot rests 110, 134 are pivoted from their unfolded positions to their folded-down positions (as indicated by arrows C in FIG. 2) and are then moved toward the sides 52, 60, respectively, of the door panels 42, 44, respectively (as indicated by arrows D in FIG. 2). In this regard, the retainer posts 88, 90 of the rail member 76 maintain the support block 96 and hence the foot rest 110 on the rail member 76 (i.e., the retainer posts 88, 90 prevent the foot rest 110 from being dismounted from the rail member 76). Likewise, the retainer posts 127, 129 of the rail member 126 maintain the support block 130 and hence the foot rest 134 on the rail member 126 (i.e., the retainer posts 127, 129 prevent the foot rest 134 from being dismounted from the rail member 126).

It should be appreciated that the present invention provides numerous advantages over the prior art discussed above. For instance, because the device 10 is portable and/or mobile, medical examinations, such as obstetric and/or gynecological examinations, can be performed alongside patient beds (e.g., hospital beds). As a result, the device 10 is particularly suitable for performing medical examinations on bed-bound patients.

It should be noted that the present invention can have numerous modifications, variations and applications. For instance, the foot support assemblies 72, 74 can be replaced with conventional stirrups. Conventional stirrups can be mounted on the door panels 42, 44 such that they retract into the door panels 42, 44 when the door panels 42, 44 are closed and they pop up from the door panels 42, 44 when the door panels 42, 44 are opened. The foot support assemblies 72, 74 can also be mounted at other locations on the cart 12. In addition, the support mat 142 can be slidably mounted to the upper end of the cart 12 such that it can be positioned on the upper end of the cart 12 when it is in its retracted position. Alternatively, the support mat 142 can be eliminated or replaced with other mechanisms. Moreover, the device 10 can be used in conjunction with different types of medical devices (e.g., patient examination tables, etc.). The device 10 can also be used in performing many different types of medical examinations (e.g., gastroenterology examinations). When performing a gastroenterology examination, the cart 12 is preferably positioned along a side of a patient's bed. Further, the device 10 can be provided with other tools and equipment, such as retractable electrical cords, etc.

It will be understood that the embodiment described herein is merely exemplary and that a person skilled in the art may make many variations and modifications without departing from the spirit and scope of the invention. All such variations and modifications are intended to be included within the scope of the invention as defined in the appended claims.

We claim:

1. A device for facilitating a medical examination, comprising a movable body having a substantially unobstructed storage compartment therein, said storage compartment extending from one lateral side of said body to an opposite lateral side of said body and from a top of said body to a bottom of said body, said body including at least one door member pivotally mounted to a front side of said body for at least partially covering said storage compartment, said at least one door member including an upper end; and supporting means mounted to said at least one door member of said body for supporting a foot of a patient during the performance of a medical examination, said supporting means including a foot rest assembly mounted on said at least one door member and including a foot rest pivotable relative to said at least one door member, said foot rest assembly having a support block movably supported on said upper end of said at least one door member, said foot rest being mounted to said support block such that it is movable conjointly with said support block along said upper end of said at least one door member.

2. The device of claim 1, wherein said foot rest is pivotally mounted to said support block such that it is pivotable between a first position, in which it extends generally upwardly from said at least one door member so as to support a patient's foot, and a second position, in which it is laid generally flat against said upper end of said at least one door member.

3. The device of claim 1, further comprising a supporting means carried by said body, said supporting member being sized and shaped so as to support a patient thereon during a medical examination.

4. The device of claim 3, wherein said supporting member is movable between an extended position, in which said supporting member extends outwardly from said body, and a retracted position, in which said supporting member does not extend substantially outwardly from said body.

5. The device of claim 4, wherein said body has a front side and a rear side, said supporting member being pivotally mounted to said rear side of said body such that said supporting member is pivotable between its said extended and retracted positions.

6. The device of claim 5, wherein said supporting member extends substantially horizontally from said rear side of said body away from said front side of said body when said supporting member is in its said extended position; and said supporting member is laid against said rear side of said body in a substantially vertical orientation when said supporting member is in its said retracted position.

7. The device of claim 6, wherein said supporting member extends substantially horizontally from said rear side of said body when said supporting member is in its said extended position such that a patient supported on said supporting member can place the patient's feet on said supporting means.

8. The device of claim 7, wherein said supporting member is sized and shaped so as to be supported on a patient's bed such that it can be maintained in its said extended position.

9. The device of claim 5, further comprising a seat member carried in said storage compartment, said seat member being removable from said storage compartment such that it can be used as a seat for medical personnel during the performance of a medical examination.

10. The device of claim 9, wherein said seat member includes a stool.

11. The device of claim 5, wherein said at least one door member includes first and second door members pivotally mounted to said front side of said body for covering said storage compartment.

12. The device of claim 5, wherein at least one door member includes a plurality of door members, one of which is pivotally mounted to said front side adjacent said one lateral side of said body, and another of which is pivotally mounted to said front side adjacent said opposite lateral side of said body, so as to cover said storage compartment.

13. A device for facilitating a medical examination, comprising: a movable body having a storage compartment therein and at least one door member movably mounted to said body for at least partially covering said storage compartment and including an upper end; and supporting means mounted to said at least one door member for supporting a foot of a patient during the performance of a medical examination, said supporting means including a foot rest assembly which is mounted on said at least one door member and which includes a foot rest pivotable relative to said at least one door member, and said foot rest assembly having a support block movably supported on said upper end of said at least one door member, said foot rest being pivotably mounted to said support block such that it is movable conjointly with said support block along said upper end of said at least one door member and such that it is pivotable between a first position, in which it extends generally upwardly from said at least one door member so as to support a patient's foot, and a second position, in which it is laid generally flat against said upper end of said at least one door member, said supporting means including a rail member fixedly mounted to said upper end of said at least one door member, said support block being movably mounted on said rail member such that it is movable relative to said upper end of said at least one door member.

14. The device of claim 13, wherein said rail member includes a plurality of holes arranged along a direction substantially parallel to said upper end of said at least one door member, said supporting means including a support member attached to said foot rest for maintaining said foot rest in its said first position, said support member including a mounting pin extending therefrom and sized and shaped so as to be received in one of said holes of said rail member for maintaining said foot rest in its said first position at a predetermined location along said rail member.

15. The device of claim 14, wherein said rail member includes a pair of retainer pins at opposing ends thereof, said support block being retained between said retainer pins.

16. A device for facilitating a medical examination, comprising a movable body having a storage compartment therein and at least one door member movably mounted to said body for at least partially covering said storage compartment; and supporting means mounted to said at least one door member for supporting a foot of a patient during the performance of a medical examination, said at least one door having first and second door panels movably mounted to said body for covering said storage compartment, each of said first and second door panels including an upper end, said supporting means including a first foot rest assembly having a first foot rest pivotable relative to said first door panel, and which is mounted on said first door panel for supporting a patient's foot, and a second foot rest assembly having a second foot rest pivotable relative to said second door panel, and which is mounted on said second door panel for supporting a patient's foot, said first foot rest assembly having a first support block movably supported on said upper end of said first door panel, said first foot rest being mounted to said first support block such that it is movable conjointly with said first support block along said upper end of said first door panel, said second foot rest assembly having a second support block movably supported on said upper end of said second door panel, said second foot rest being mounted to said second support block such that it is movable conjointly with said second support block along said upper end of said second door panel.

17. The device of claim 16, wherein said first foot rest is pivotally mounted to said first support block such that it is pivotable between a first position, in which it extends generally upwardly from said upper end of said first door panel so as to support a patient's foot, and a second position, in which it is laid generally flat against said upper end of said first door panel; and wherein said second foot rest is pivotally mounted to said second support block such that it is pivotable between a third position, in which it extends generally upwardly from said upper end of said second door panel so as to support a patient's foot, and a fourth position, in which it is laid generally flat against said upper end of said second door panel.

18. The device of claim 17, wherein said first foot rest assembly includes a first rail member fixedly mounted to said upper end of said first door panel, said first support block being movably mounted on said first rail member such that it is movable relative to said upper end of said first door panel; and wherein said second foot rest assembly includes a second rail member fixedly mounted to said upper end of said second door panel, said second support block being movably mounted on said second rail member such that it is movable relative to said upper end of said second door panel.

19. The device of claim 18, wherein said first rail member includes a plurality of first holes arranged along a direction substantially parallel to said upper end of said first door panel, said first foot rest assembly including a first support member attached to said first foot rest for maintaining said first foot rest in its said first position, said first support member including a first mounting pin extending therefrom and sized and shaped so as to be received in one of said first holes of said first rail member for maintaining said first foot rest in its said first position at a predetermined location along said first rail member; and wherein said second rail member includes a plurality of second holes arranged along a direction substantially parallel to said upper end of said second door panel, said second foot rest assembly including a second support member attached to said second foot rest for maintaining said second foot rest in its said third position, said second support member including a second mounting pin extending therefrom and sized and shaped so as to be received in one of said second holes of said second rail member for maintaining said foot rest in its said third position at a predetermined location along said second rail member.

20. The device of claim 19, wherein said first rail member includes a pair of first retainer pins at opposing ends thereof, said first support block being retained between said first retainer pins; and wherein said second rail member includes a pair of second retainer pins at opposing ends thereof, said second support block being retained between said second retainer pins.

21. The device of claim 16, further comprising first and second wheels mounted to said first door panel and said second door panel, respectively, for movably supporting said first and second door panels on a support surface.

* * * * *